(12) United States Patent
Otani et al.

(10) Patent No.: US 9,733,194 B2
(45) Date of Patent: Aug. 15, 2017

(54) METHOD FOR REVIEWING A DEFECT AND APPARATUS

(71) Applicants: Hitachi High-Technologies Corporation, Minato-ku, Tokyo (JP); The University of Tokyo, Bunkyo-ku, Tokyo (JP)

(72) Inventors: Yuko Otani, Tokyo (JP); Shunji Maeda, Tokyo (JP); Yuta Urano, Tokyo (JP); Toshifumi Honda, Tokyo (JP); Takehiro Hirai, Tokyo (JP); Satoru Takahashi, Tokyo (JP); Kiyoshi Takamasu, Tokyo (JP)

(73) Assignees: Hitachi High-Technologies Corporation, Tokyo (JP); The University of Tokyo, Tokyo (JP)

( * ) Notice: Subject to any disclaimer, the term of this patent is extended or adjusted under 35 U.S.C. 154(b) by 21 days.

(21) Appl. No.: 14/799,741

(22) Filed: Jul. 15, 2015

(65) Prior Publication Data

US 2016/0018340 A1 Jan. 21, 2016

(30) Foreign Application Priority Data

Jul. 15, 2014 (JP) ................................. 2014-145199

(51) Int. Cl.
*G01N 21/00* (2006.01)
*G01N 21/88* (2006.01)
*G01N 21/95* (2006.01)
*G01N 21/956* (2006.01)

(52) U.S. Cl.
CPC ..... *G01N 21/8806* (2013.01); *G01N 21/8851* (2013.01); *G01N 21/9501* (2013.01); *G01N 21/956* (2013.01); *G01N 2021/8822* (2013.01); *G01N 2021/8848* (2013.01); *G01N 2021/8867* (2013.01)

(58) Field of Classification Search
CPC ............... G01M 11/3145; G01N 21/47; G01N 21/9501; G01N 21/94; G01N 21/956; G01N 2021/8822; G01N 21/8806
USPC ........................................... 356/237.2–237.6
See application file for complete search history.

(56) References Cited

U.S. PATENT DOCUMENTS

| | | | | |
|---|---|---|---|---|
| 2003/0231297 | A1* | 12/2003 | Endo .................. | G01M 11/3145 356/73.1 |
| 2007/0121106 | A1* | 5/2007 | Shibata .............. | G01N 21/8806 356/237.2 |
| 2009/0279081 | A1* | 11/2009 | Urano ................ | G01N 21/9501 356/237.5 |

(Continued)

FOREIGN PATENT DOCUMENTS

JP 2011-106974 A 6/2011

*Primary Examiner* — Tarifur Chowdhury
*Assistant Examiner* — Isiaka Akanbi
(74) *Attorney, Agent, or Firm* — Miles & Stockbridge P.C.

(57) ABSTRACT

A method for reviewing a defect including a light capturing step that illuminates a sample with light under plural optical conditions, while varying only at least one of illumination conditions, sample conditions, or detection conditions, and detects plural lights scattering from the sample; a signal obtaining step that obtains plural signals based on the lights detected; and a processing step that discriminates a defect from noise according to a waveform characteristic quantity, an image characteristic quantity, or a value characteristic quantity created using the signals and derives the coordinates of defect.

15 Claims, 11 Drawing Sheets

(56) References Cited

U.S. PATENT DOCUMENTS

| | | | |
|---|---|---|---|
| 2012/0050729 A1* | 3/2012 | Mitomo | G01N 21/94 356/237.1 |
| 2012/0274931 A1 | 11/2012 | Otani et al. | |
| 2013/0002849 A1* | 1/2013 | Sakai | G06T 7/001 348/86 |
| 2013/0114078 A1* | 5/2013 | Honda | G01N 21/9501 356/364 |
| 2013/0148116 A1* | 6/2013 | Tanaka | G01N 21/95623 356/237.5 |
| 2013/0148859 A1* | 6/2013 | Inoue | H04N 13/0018 382/106 |
| 2013/0329039 A1* | 12/2013 | Sakai | G01N 21/9501 348/126 |

* cited by examiner

F I G. 1 0
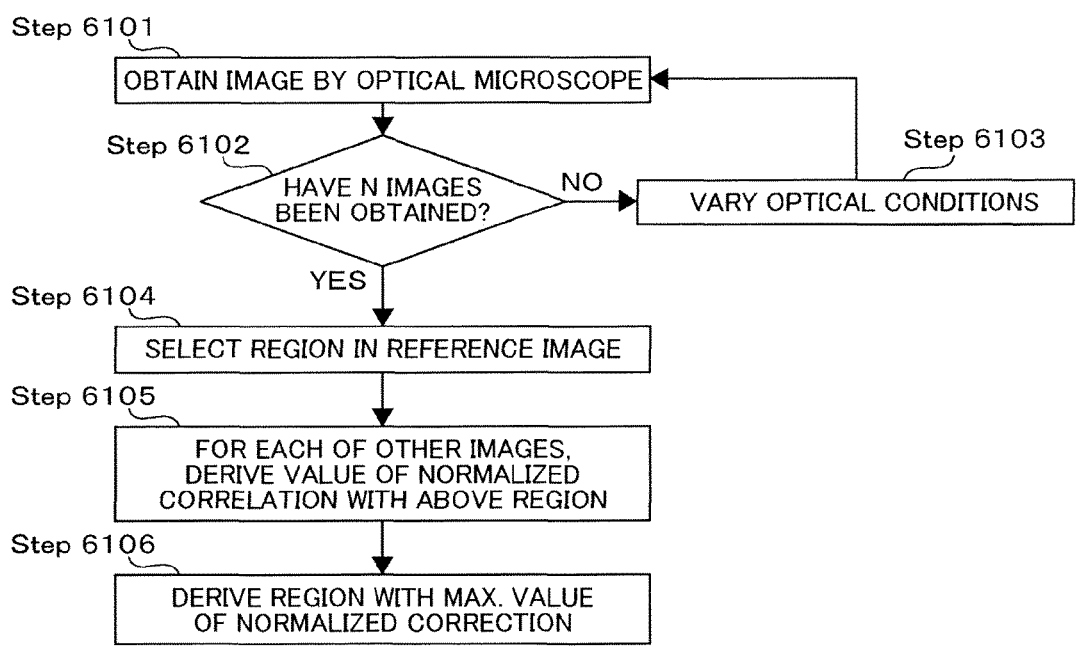

METHOD FOR REVIEWING A DEFECT AND APPARATUS

BACKGROUND

The present invention relates to a method for reviewing a defect and apparatus for reviewing a defect or the like which is present on or near the surface of a sample and has been detected by a defect inspection apparatus.

For example, in a process of manufacturing semiconductor devices, if any of foreign materials or pattern defects such as a short circuit and wiring disconnection (which will be generically termed defects, hereinafter) is present on a semiconductor substrate (wafer), it may cause a fault such as a wiring insulation fault or a short circuit. As circuit patterns which are formed on a wafer become finer, finer defects may cause a capacitor insulation fault or gate oxide film breakage. These defects are introduced in various conditions and due to various causal agents such as those which are generated from a moving element of conveying equipment, those which are generated from a human body, those which are generated through reaction inside treatment equipment with a process gas, and those mixed in a chemical or material. Thus, it is important for mass production of semiconductor devices to detect a defect generated during a manufacturing process, identify a source of generating the defect as early as possible, and hold back the production of faulty devices.

A method so far applied for pursuing a cause of generating a defect is such that the position of a defect is first detected by a defect inspection apparatus, the defect is reviewed in detail by a reviewing apparatus such as a SEM (Scanning Electron Microscope) and categorized, and a cause of generating the defect is presumed by comparison against a database in which results of inspection obtained in all processes of manufacturing have been stored.

Here, the defect inspection apparatus is an optical defect inspection apparatus which irradiates the surface of a semiconductor substrate with laser, makes a dark-field review of light scattering from a defect, and identifies the position of the defect, or an optical external view inspection apparatus or SEM-type inspection apparatus which detects a brightfield optical image of a semiconductor substrate by lamp light, laser, or electron beam irradiation and compares this image with reference information, thereby identifying the position of a defect on the semiconductor substrate.

There is also a method as follows. Using information representing the position of a defect on a sample, which has been detected by any other inspection apparatus, detecting the defect position on a sample is performed by an optical microscope installed in a SEM-type apparatus for reviewing a defect. After correcting the defect position information obtained through the detection by the other inspection apparatus, reviewing the defect in detail is performed by the SEM-type apparatus for reviewing a defect.

In Japanese Unexamined Patent Application Publication No. 2011-106974, there is described enhancing the sensitivity of a dark-field type optical microscope by locating a spatially distributed filter on or near the pupil plane of an optical system for detection.

There is also a sensitivity enhancement method by using an image in which noise is suppressed, obtained by combining images obtained under different optical conditions.

SUMMARY

In recent LSI manufacturing, as circuit patterns become finer in response to higher integration needs, defects to be detected also become finer. Accordingly, an optical defect inspection apparatus is required to detect a defect with finer dimensions. Scattering by an object that is sufficiently smaller than the wavelength of illuminating light is Rayleigh scattering. Because the intensity of this scattering light is proportional to the sixth power of the diameter of a particle that scatters light, the defect scattering light drastically decreases along with size shrinkage of a defect under measurement and might be buried in noise. As causes of noise that impedes defect detection, there are light scattering from a rough surface of a sample and noise attributed to sensors and circuits including speckle noise and heat noise. Thus, even if high intensity illumination is used so that a sufficient defect scattering light can be ensured against noise attributed to sensors and circuits and time for scattering light accumulation is lengthened, light scattering from a microparticle is buried in roughness scattering light and cannot be detected.

As a method for separating defect scattering light from roughness scattering light, there is a method which exploits that these scattering lights have different polarized light intensity distributions and utilizes a filter (which is a mask, polarizer, or wave plate) located on the pupil plane so that the filter will selectively transmit only light scattering from a defect, thus eliminating roughness scattering light (Japanese Unexamined Patent Application Publication No. 2011-106974). However, for higher sensitivity, it is required to increase the difference between defect scattering light transmissivity and roughness scattering light transmissivity of the filter, and filter transmittance conditions (scattering direction and polarization) are tightened. In consequence, although the ratio of defect scattering light to roughness scattering light is boosted, due to a decrease in the defect scattering light transmissivity of the filter, the influence of noise attributed to sensors and circuits increases and a defect cannot be visualized.

To increase the amount of defect scattering light captured by sensors, inter alia, shortening illuminating light wavelength and enhancing the numerical aperture (NA) of lenses for detection are implemented. However, shortening illuminating light wavelength has technical and apparatus cost limitations. Although liquid immersion and meta-materials with a negative refractive index are available for enhancing the NA of lenses for detection, liquid immersion is hard to use in inspection of semiconductors and putting meta-materials into practical use is technically difficult.

There is a need for a technique for separating defect scattering light from roughness scattering light and visualizing a defect other than the technique of filtering on the pupil plane.

In Japanese Unexamined Patent Application Publication No. 2011-106974, no description is provided about a method for visualizing a defect using multiple images.

To solve problems noted above, the present invention provides a method for reviewing a defect including a light capturing step that illuminates a sample with light under plural optical conditions, while varying only at least one condition of illumination conditions, sample conditions, or detection conditions, and detects plural lights scattering from the sample; a signal obtaining step that obtains plural signals based on the plural lights detected; and a processing step that discriminates a defect from noise according to a waveform characteristic quantity, an image characteristic quantity, or a value characteristic quantity created using the plural signals and derives coordinates of the defect as well as an a apparatus for reviewing a defect.

According to the present invention, it is possible to provide a method for reviewing a defect and apparatus with enhanced throughput.

These features and advantages of the invention will be apparent from the following more particular description of preferred embodiments of the invention, as illustrated in the accompanying drawings.

BRIEF DESCRIPTION OF THE DRAWINGS

FIG. 10 is a flowchart explaining an example of a procedure for determining the same location on a sample according to an embodiment of the present invention;

DESCRIPTION OF THE PREFERRED EMBODIMENTS

The present invention relates to a defect detection method and apparatus making it possible to detect a fine defect more rapidly when detecting a defect using a dark-field optical microscope as well as a method and apparatus for reviewing a defect which has been detected by another inspection apparatus through the use of the foregoing defect detection apparatus.

With the aid of the drawings, embodiments of the present invention will be described below.

First Embodiment

Figure 1:
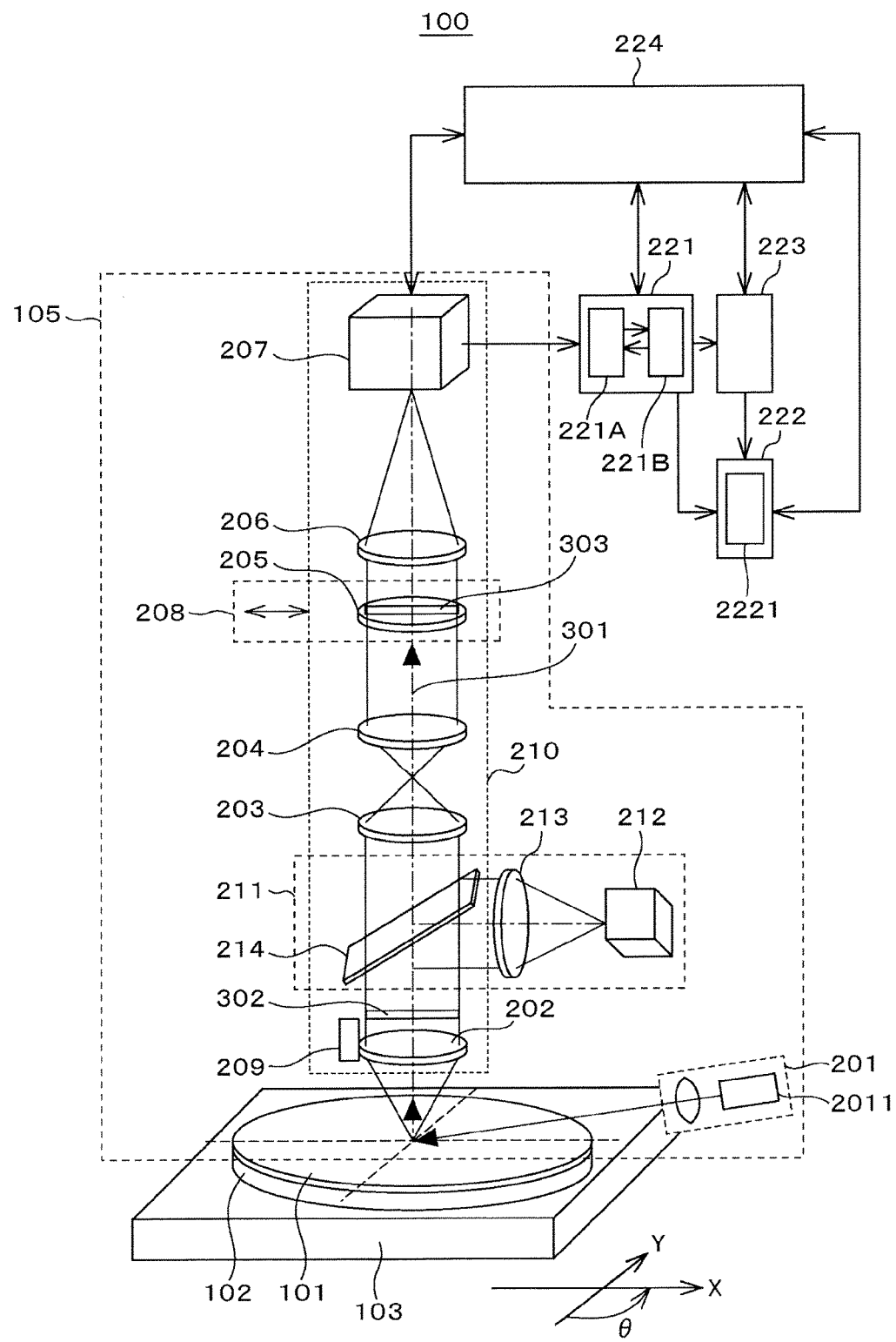
FIG. 1 is a structural diagram depicting an example of structure of an optical microscope according to an embodiment of the present invention.

First, an embodiment of a defect detection apparatus 100 using a dark-field optical microscope according to the present invention is described with FIG. 1.

The defect inspection apparatus 100 according to the present embodiment depicted in FIG. 1 includes an optical microscope 105, a signal processing unit 221, an image display unit 222, a signal storage unit 223, and a control unit 224. The control unit 224 is connected to an external data processing device by a communication means which is not depicted.

The optical microscope 105 includes an illumination unit 201, an object lens 202 for capturing light scattering from a sample 101 and making a bright-field review, an object lens height control mechanism 209, a half mirror 214 for letting in illuminating light necessary for a bright-field review, an illumination lens 213, a bright-field light source 212, an imaging optical system 210 which transmits scattering light captured by the object lens 202 to an imaging element 207 to create an image of a sample 101 using the scattering light, and the imaging element 207. In conjunction with the optical microscope, the following are appropriately used: the signal processing unit 221 which processes a signal obtained by the imaging element 207; the image display unit 222 which displays a signal obtained by the signal processing unit 221; and the signal storage unit 223 which stores a signal obtained by the signal processing unit 221. In addition, the imaging optical system 210 appropriately includes a spatially distributed optical element (filter) 205 and a spatially distributed optical element switching mechanism 208. The signal processing unit includes a sub-unit 221A which processes obtained data and a sub-unit 221B which performs processing by making reference to and comparison against stored data which has previously been obtained and stored in a library.

As the bright-field light source 212, a lamp or laser can be used. When laser is used, the condenser lens 213 may be dispensed with and illumination is made brighter by replacing the half mirror 214 with a dichroic mirror, so that a larger amount of scattering light can be guided to the imaging element 207.

A ratio between light reflection and transmission of the half mirror 214 may be optional. However, if it is ensured that the bright-field light source 212 provides sufficient intensity of light, a structure in which a larger amount of light scattering from a defect is guided to the imaging optical system 210 and the imaging element 207 is preferable. A light-field illumination unit may be movable so that it may get out of an optical axis 301 when it is not used. In that case, there is an advantage in which a larger amount of scattering light can be guided to the imaging element 207.

The illumination optical unit 201 includes the following components which are appropriately used: a light source 2011 and a condenser lens to converge and deliver a light beam which is emitted from the light source 2011 onto a sample 101.

As the structure of the height control mechanism 209, for example, the following can be used: a structure adapted to move the object lens using a piezo element; a structure adapted to move the object lens in a Z direction (along the optical axis 301 the imaging optical system 210) along a linear guide using a stepping motor and a ball screw; or a structure adapted to move the object lens in the Z direction along the linear guide using an ultrasonic motor and a ball screw.

The imaging element 207 may be disposed in a conjugated position with respect to the surface of a sample or the pupil plane of the object lens. The imaging optical system 210 includes the following components which are appropriately used: lenses 203, 204 which extract the pupil plane 302 of the object lens 202; an imaging lens 206 which converges light onto the imaging element 207 to create an image of a sample 101; and a filter 205 which is inserted on or near the pupil plane 303 of the object lens 202 extracted by the lenses 203, 204.

In the present embodiment, such a structure is adapted that a filter holder 208 which holds plural filters 205 with different characteristics which are switchable from one to another is inserted on or near the pupil plane 303. The filter 205 may not be required to be disposed on the optical axis 301 of the imaging optical system 210.

The imaging element 207 is connected to the image processing unit 221.

The lenses 203, 204 are used to extract the pupil plane 302 of the object lens 202 outside and form it inside the imaging optical system 210.

It is possible to drive the filter holder 208 and a filter 205 selected out of plural filters 205 held in the filter holder 208 is inserted on the pupil plane 303 extracted inside the imaging optical system 210.

When making a bright-field review or when no filter 205 is used, a position to be inserted on the pupil plane within the filter holder 208 should be set in a position where no filter 205 is installed to avoid disturbance of an image obtained. Alternatively, the above position should be switched to a position where a parallel plate glass which is as thick as a filter 205 is installed within the filter holder 208. The reason why the parallel plate glass which is as thick as a filter 205 is installed is to avoid the changes of the light path length by the removal of a filter 205 and causes a shift of the converge point of an image of the sample 101 from the imaging element 207. Alternatively, instead of installing the parallel plate glass, a mechanism may be used which adjusts the position of the imaging lens 206 for light convergence or the imaging element 207 so that an image will be created on the imaging element 207.

In the present embodiment, a set of four lenses, namely, the object lens 202, lenses 203, 204, and imaging lens 206 is used for light convergence onto a detection plane of the imaging element 207 to create an image of a sample 101. While, in the present embodiment, the imaging optical system 210 uses two lenses 203, 204 in addition to the object lens 202 and the imaging lens 206, only either one of the lenses 203, 204 may be used and can be selected appropriately. According to the present embodiment, in the structure depicted in FIG. 1, the pupil plane 302 of the object lens 202 is reproduced as an image of the pupil plane 303 through the use of the lenses 203, 204. However, in a case where the object lens 202 of a type which allows a filter to be located on the pupil plane 302 is used or in a case of where a filter is used for which it is not required to locate a filter 205 on or near the pupil plane 302 or pupil plane 303, as is the case for linear polarized light detection, light convergence onto the imaging element 207 to create an image may be accomplished only with the object lens 202 and the imaging lens 206 without using the lenses 203, 204.

Figure 2:
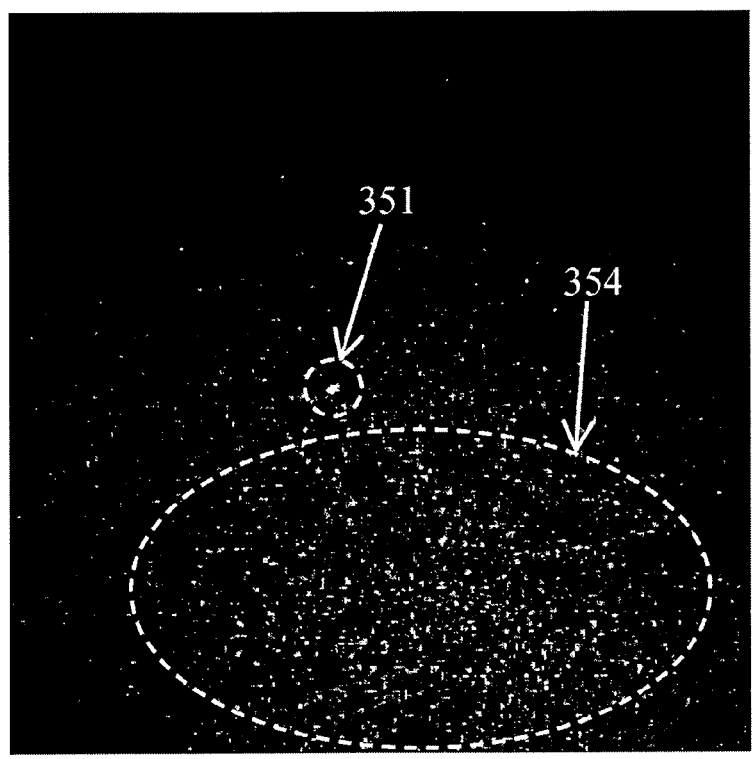
FIG. 2 is a diagram explaining an example of an image that is obtained according to an embodiment of the present invention.

Then, roughness scattering light in a dark-filed image, which interfere with defect detection, is described with FIG. 2. A dark-field image 355 is an image formed by the light scattering from in the neighborhood of a defect with size of several tens of nanometers. A bright point 351 in FIG. 2 represents an image made by light scattering from the defect and other bright points 354 are an image made by light scattering from roughness. The image made by light scattering from the defect is an image made by an electromagnetic wave generated by polarization of the defect that is oscillated by illuminating light (electromagnetic wave) and the defect scattering light is only generated from the defect.

On the other hand, the image made by light scattering from roughness is a speckle pattern image produced by interference between beams of scattering light generated by polarization of an irregular surface with irregularity ranging several angstroms (Å) across an entire area illuminated by illuminating light. Thus, its pattern changes very sensitively to optical conditions such as an illuminating light incident angle and polarization.

Light scattering from a fine defect is more stable than a roughness scattering light image. Thus, a composite image in which a speckle pattern is suppressed should be produced by integrating or summing multiple images obtained with an optical condition being varied and defect detection should be performed using the composite image. However, because an extremely fine defect is sensitive to optical conditions, varying an optical condition could result in disappearance of a bright point which is made by light scattering from the defect, as is the case for a speckle pattern derived from roughness. If an optical condition is varied but to a very small extent, a speckle pattern derived from roughness, which is desired to change, would be nearly unchanged and it would be difficult to visualize a defect buried in the speckle pattern even in a composite image produced. However, a defect scattering light image and a speckle pattern image derived from roughness scattering light have different levels of sensitivity to optical condition variation.

Therefore, the present invention discloses a method that, using multiple images under different optical conditions obtained with an optical condition being varied continuously, derives a relative inter-image change of a characteristic quantity which is obtained from each image, discriminates defect scattering light from roughness scattering light through the use of the relative inter-image change, actualize a defect, and derives the defect coordinates.

Figure 3:
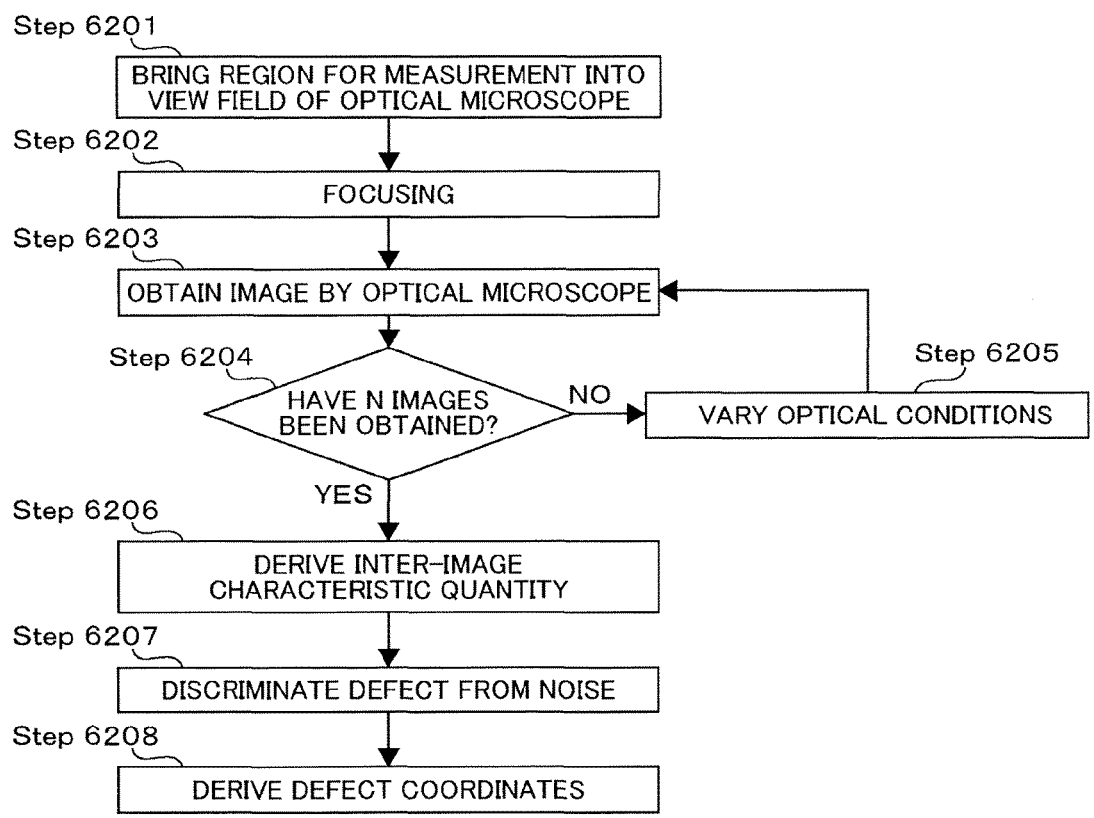
FIG. 3 is a flowchart illustrating an example of a procedure for deriving defect coordinates in an optical inspection apparatus according to an embodiment of the present invention.

An example of a processing flow for deriving defect coordinates using multiple images obtained with an optical condition being varied continuously is described with reference to FIG. 3.

A first step is moving a stage 103 to bring a region for measurement on the surface of a sample 101 into the view field of the optical microscope 105 (Step 6201). A next step is focusing by moving the object lens 202 with the height control mechanism 209 (Step 6202). A next step is obtaining an image by the imaging element 207 of the optical microscope 105 (Step 6203). If N images necessary for discriminating a defect from noise are not yet obtained (Step 6204, NO), obtaining an image by the imaging element 207 of the optical microscope 105 (Step 6203) is repeated, while varying an optical condition (Step 6205). This is continued until necessary N images have been obtained. Once N images with an optical condition being varied have been obtained (Step 6204, YES), a step that follows is deriving an inter-image characteristic quantity using the N images (Step 6206), followed by discriminating a defect from roughness through the use of the derived inter-image characteristic quantity (Step 6207) and deriving the coordinates of the defect discriminated from noise (Step 6208).

As optical conditions which may be varied, conceivable are spatial conditions such as distance between the focal position of the object lens and a sample (hereinafter referred to as "height") and the stage position, illumination conditions such as illuminating light wavelength and polarization, direction angle, and incident angle, and detection conditions such as wavelength for detection, polarization, optical characteristics of a pupil filter, sensor position, sensor sensitivity, and accumulation time. By varying any parameter of these multiple optical conditions, it is possible to vary an optical condition continuously. For example, if height is selected as an optical condition to be varied when obtaining images, an available way is to move the stage 103 up and down or move the object lens 202 up and down with the height control mechanism 209.

If illumination polarization is to be varied, an available way is to rotate a ½ wavelength plate disposed in the light path of the illumination optical system in a vertical direction with respect to the optical axis. If polarization for detection is to be varied, an available way is to rotate a polarizer or polarized beam splitter disposed in the light path of the optical system for detection in a vertical direction with respect to the optical axis. The pupil filter is an optical filter for boosting the ratio of defect scattering light to roughness scattering light described in Japanese Unexamined Patent Application Publication No. 2011-106974. Another available way is to obtain images under different optical conditions by switching between or among pupil filters having different optical characteristics. An amount and a direction of optical condition variation are selected and controlled by the processing unit 221.

When multiple images are obtained with an optical condition being varied continuously, an extent in which the optical condition is to be varied should be an extent in which defect scattering light does not disappear in at least two images. This is because it is necessary to trace a relative change of the bright points of defect scattering light and roughness scattering light. For example, when two images are obtained with an optical condition being varied, if a bright point derived from defect scattering light is present under one condition, but it is absent under another condition, it cannot be determined that the bright point is a defect because bright points derived from roughness scattering light make a similar change.

Bright points derived from roughness scattering light, which are present under one condition, may or may not disappear under another condition and new ones may appear at different coordinates on a wafer. If a bright point of defect scattering light is present in at least two images among multiple images obtained under different optical conditions, the bright point of defect scattering light may disappear in the remaining images. An extent of optical condition variation in which a bright point derived from defect scattering light is present may also be a parameter for discriminating a defect from roughness.

For example, if height is selected as an optical condition to be varied, as an extent in which the optical condition is varied, images should be obtained in a variation extent in which a bright point derived from defect scattering light does not disappear within a focal depth of the optical system for detection and which includes at least two conditions of height. Given the same illumination intensity density, the intensity of a bright point derived from defect scattering light is nearly unchanged, if the bright point is within the focal depth of the optical system for detection. On the other hand, the intensity of bright points derived from roughness scattering light changes. If images are obtained under at least two conditions (two different heights) within the focal depth of the optical system for detection, other images may be obtained out of the focal depth of the optical system for detection. If a bright point is present in the same position even when height has been varied far out of the range of the focal depth of the optical system for detection, it is considered as, e.g., noise attributed to a sensor.

Figure 4:
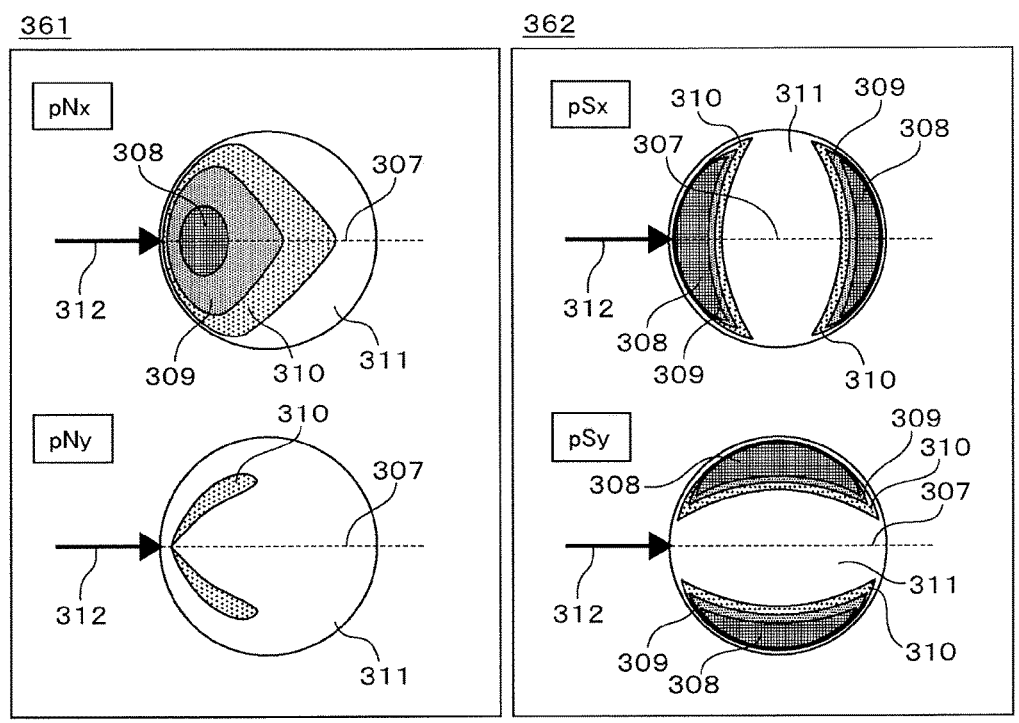
FIG. 4 is a diagram explaining examples of polarized light intensity distributions of defect scattering light and roughness scattering light.

Then, using FIG. 4, an explanation is provided about an amount of optical condition variation between images, when obtaining images. FIG. 4 depicts examples of polarized light components of light scattering from a defect with a diameter of 18 nm and roughness scattering light. Both are upward projections of a scattering hemisphere. An image 361 is of light scattering from roughness and an image 362 is of light scattering from the defect; of each illustration, an upper part represents intensity distribution of X-polarized light and a lower part represents intensity distribution of Y-polarized light. In the illustrations, a line 312 denotes an illuminating light incident direction, an axis 307 denotes an illuminating light incident plane, a region 308 denotes a high intensity portion, a region 309 denotes a slightly high intensity portion, a region 310 denotes a slightly low intensity portion, and a region 311 denotes a low intensity portion. In this regard, images should be obtained in multiple conditions of polarization for detection including two conditions of X-polarized light and Y-polarized light and polarization directions interpolating between them.

In FIG. 4, the intensity of the X-polarized scattering light of roughness scattering light is stronger than the Y-polarized light. Consequently, if an attempt is made to eliminate a speckle pattern and visualize a defect by using only the images obtained in two optical conditions of X-polarized and Y-polarized light, a bright point derived from a defect appearing in the Y-polarized light image can disappear in the X-polarized light image and not only a speckle pattern, but also the defect may be eliminated when the above two images are combined. Then, a case where optical condition variation between images is small is explained. Bright points derived from roughness scattering light are made up of combinations of low-frequency and high-frequency components of spatial frequencies from irregularities of a rough surface. Thus, among bright points derived from the same roughness scattering light, there are bright points that are invulnerable to optical condition variation and bright points that are vulnerable to optical condition variation. Thus, if optical condition variation between images is small, it is impossible to make discrimination between light scattering from a defect and light scattering from roughness which is invulnerable to optical condition variation.

Therefore, it is needed to visualize a defect by tracing an inter-image change of a characteristic quantity such as brightness by using dark-field images obtained in polarization conditions interpolating between X-polarized light and Y-polarized light in addition to X-polarized light detection and Y-polarized light detection.

When obtaining images, it is necessary to determine parameters of optical condition variation between images such as the number of images to be obtained, an amount (pitch) of optical condition variation between images, a maximum amount of optical condition variation, and an optical condition to be varied. Examples of ways to determine such parameters of optical condition variation are described below. One possible way is to use standard particles dispersed on a sample or an actual defect or the like, obtain dark-field images of them with an optical condition being varied, derive a profile and tendency of change depending on the optical condition variation, and store them as parameters specific to apparatus. Another possible way is to use a sample for inspection, obtain dark-field images of it with an optical condition being varied, derive parameters of optical condition variation for which roughness scattering light images sufficiently change depending on optical condition variation, and determine parameters of optical condition variation.

Change of defect scattering light images depending on optical condition variation is determined by an extent of optical condition variation, an amount of variation, defect conditions (such as size, type, shape, and orientation to an illuminating light incident direction), and apparatus. Thus, it is effective to use a standard sample and obtain dark-field images of it with possible values of an extent of optical condition variation, an amount of variation, defect conditions and acquire in advance parameters of optical condition variation specific to apparatus. In this regard, it is not required to obtain dark-field images of a standard sample with all possible values of optical conditions and conditions of a defect to be detected. Parameters of optical condition variation may be derived by computation through the use of aberration information and scattering simulation in the apparatus structure and the optical system for detection.

If parameters of optical condition variation for which roughness scattering light images sufficiently change depending on optical condition variation are used, multiple dark-field images of a possible sample for review may be obtained with an optical condition parameter being changed and parameters of optical condition variation may be determined from the obtained images and stored in advance as the parameters specific to apparatus. Alternatively, when actual inspection is carried out, dark-field images of a sample for inspection may be obtained with an optical condition being varied and parameters of optical condition variation may be determined from the obtained images.

It is also conceivable to use results of SEM review and feed them back to the operation for setting parameters of optical condition variation to optimize conditions. For example, defect candidates derived from multiple dark-field images obtained with initially set parameters of optical condition variation are reviewed by SEM, but a success rate of defect detection is low. In such a case, defect scattering light and roughness scattering light would behave similarly in response to an optical condition variation. Thus, it is conceivable, for example, to set a wider extent of optical condition variation and to increase the number of images to be obtained. Alternatively, it is conceivable to change the mode of an optical condition to be varied to another optical condition that is more beneficial for discrimination.

Inter-image characteristic quantity and a method for discriminating a defect from noise are described below.

Inter-image characteristic quantity is an image characteristic quantity, a waveform characteristic quantity, a value characteristic quantity, or a combination of these quantities, including an inter-image optical condition variation extracted from multiple images. An image characteristic quantity includes three-dimensional data having values on two dimensions (plane). A waveform characteristic quantity includes two-dimensional data having values on one dimension (line). A value characteristic quantity includes one-dimensional data having a value on a point.

Figure 5:
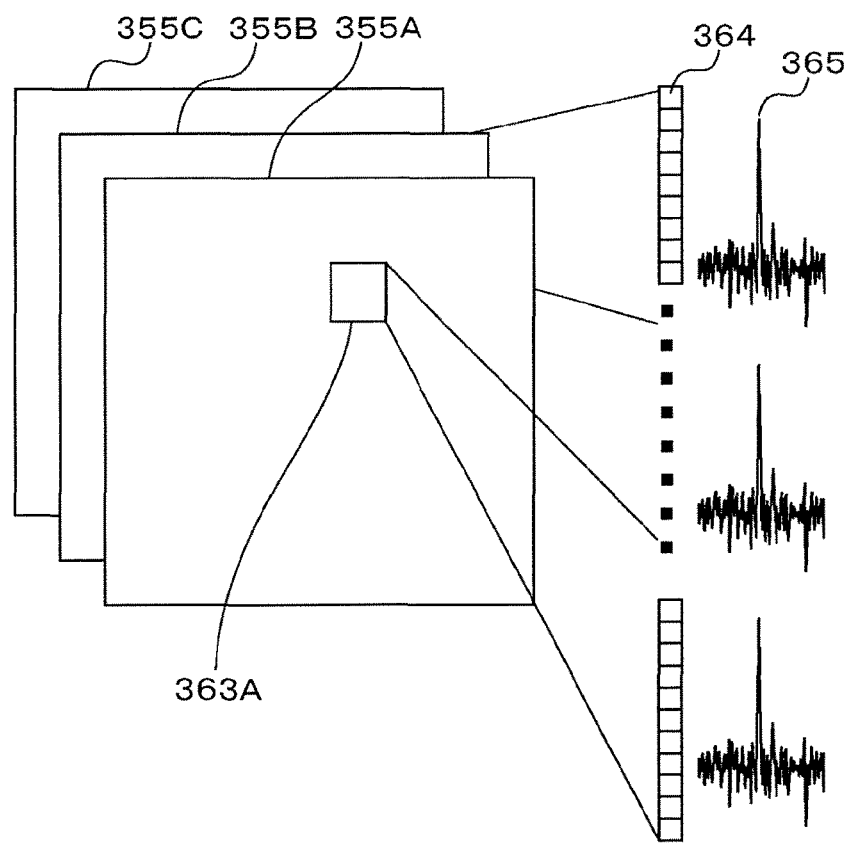
FIG. 5 is a diagram explaining an example of waveform characteristic quantity according to an embodiment of the present invention.

FIG. 5 depicts an example of a waveform characteristic quantity. Corresponding regions 363A, 363B, 363C are clipped out from dark-field images 355A, 355B, 355C obtained under different optical conditions and a series of output values of all pixels 364 in each clipped-out region 363 is brought into line. A thus obtained waveform signal 365 may be taken as an inter-image characteristic quantity. Although three images are used in FIG. 5, the number of dark-field images for use is not so limited. The clipped-out regions 363A, 363B, 363C may be taken as an image characteristic quantity without transformation to waveforms. In addition, two-dimensional images created by Fourier transform of the clipped-out regions 363 may be taken as an image characteristic quantity or what is made by serial arrangement of every image data created by Fourier transform of the clipped-out regions 363 may be taken as a waveform characteristic quantity.

As a value characteristic quantity, within a region 363 clipped out from a dark-field image 355, for example, a bright spot with brightness at or above a threshold, its area and shape, the center of gravity of brightness in the spot, and average brightness, a characteristic quantity distribution, etc. may be taken as a value characteristic quantity. A relative change of a value characteristic quantity between optical conditions may be used as a waveform characteristic quantity. Likewise, what is made by parallel arrangement of every image data representing a relative change of a waveform characteristic quantity between optical conditions may be taken as an image characteristic quantity or what is made by serial arrangement thereof, as in FIG. 5, may be taken as a waveform characteristic quantity. Besides, the coordinates and characteristic quantity of a point having a maximum characteristic quantity within a range in a waveform characteristic quantity may be taken as a bright point characteristic quantity. Although the example in which clipped-out regions 363 of the obtained dark-field images 355 are used is described above, the clipped-out regions 363 may be equal to the dark-field images 355.

Discrimination is made of a defect from noise including roughness scattering light using an inter-image characteristic quantity described above. Discrimination methods include, among others, inter-image characteristic quantity pattern matching and a method using a discrimination boundary for discriminating a defect from noise in a characteristic quantity space.

For setting a matching pattern and a discrimination boundary, a possible way is to set them through the use of dark-field images obtained in advance using a standard sample. One possible way is to use standard particles dispersed on a sample or an actual defect or the like, obtain dark-field images of them with an optical condition being varied, derive a defect pattern and a discrimination boundary, and store them as parameters specific to apparatus. Change of defect scattering light images depending on optical condition variation is determined by an extent of optical condition variation, an amount of variation, defect conditions (such as size, type, shape, and orientation to an illuminating light incident direction), and apparatus. Thus, it is effective to use a standard sample and obtain dark-field images of it with possible values of an extent of optical condition variation, an amount of variation, defect conditions and acquire in advance a defect pattern and a discrimination boundary for each apparatus.

In this regard, it is not required to obtain dark-field images of a standard sample with all possible values of optical conditions and conditions of a defect to be detected. A defect pattern and a discrimination boundary may be derived by computation through the use of aberration information and scattering simulation in the apparatus structure and the optical system for detection. It is also conceivable to use results of SEM review and feed them back to the operation for setting a defect pattern and a discrimination boundary to optimize them. Doing so enhances the accuracy of discrimination. A description will separately be provided about optimizing a defect pattern and a discrimination boundary using SEM review results by way of FIG. 12.

In a case where a characteristic quantity changes but to a rather small extent, depending on optical condition variation, because of a different type of a defect, a defect pattern and a discrimination boundary may be derived through the use of a particular standard particle (such as, e.g., a spherical polystyrene particle) and a defect that is not buried in light scattering from roughness present on a sample under measurement. In a case where a characteristic quantity changes but to a rather large extent, depending on optical condition variation, because of a different type of a defect, multiple defect parameters and discrimination boundaries obtained under multiple defect conditions may be used. According to a defect type desired to be detected, a defect pattern and a discrimination boundary that are beneficial for discriminating the defect type from other types may be used. A beneficial discrimination method may be selected by using inspection output data obtained beforehand using a defect inspection apparatus or the like.

Spatial displacement is considered as an optical condition for which an inter-image characteristic quantity changes to a rather small extent depending on the optical condition. For example, when displacement occurs in a vertical direction to the optical axis of the optical system for detection (i.e., a horizontal direction), defect types do not affect change of the brightness value of a defect depending on optical condition variation. In this case, a spot for which signal value change depending on optical condition variation is nearly constant can be determined as a defect.

Then, a description is provided about a case where height has been selected as an optical condition to be varied. Possible causes of changing defect scattering light images when the height relative to the defect is varied are aberration of the optical system for detection and deviation of a height displacement direction from the optical axis of the optical system for detection among others. If the optical system for detection is the one in which the influence of aberration of the optical system is nearly ignorable and if defect scattering light images shift due to deviation of the height displacement direction from the optical axis of the optical system for detection, defect conditions do not affect change of defect scattering light images. Thus, a matching pattern and a discrimination boundary may be determined through the use of images made by light scattering from a standard particle and a defect that is not buried in light scattering from roughness present on a sample under measurement. If the influence of aberration of the optical system for detection is large and defect types largely affect an inter-image characteristic quantity, multiple matching patterns and discrimination boundaries which are different for each defect condition may be used.

Besides, a beneficial discrimination method may be selected by using inspection output data obtained beforehand using a defect inspection apparatus or the like. For example, one available way is to use matching patterns and discrimination boundaries which are different for each defect size by using defect size data included in the inspection output data.

Using the foregoing methods, discriminating defect scattering light from noise and deriving defect coordinates and a defect likelihood value for each region judged as a defect are performed. As defect coordinates, it is conceivable to use, but not limited to, the center of gravity of brightness or its maximum value in a defect region. A defect likelihood value indicates a probability that a defect candidate judged as a defect is a defect. As a defect likelihood value, it is conceivable to use, e.g., a distance from a discrimination boundary between a defect and noise to an image characteristic quantity in the region in question in a characteristic quantity space.

When outputting dark-field images, dark-field-like images in which a region judged as a defect is emphasized may be output to impress the shape, size, and brightness of a defect on human sight. As an emphasizing method, conceivable is applying a gain from 0 to 1 to an image other than a region judged as a defect among others.

Figure 6:
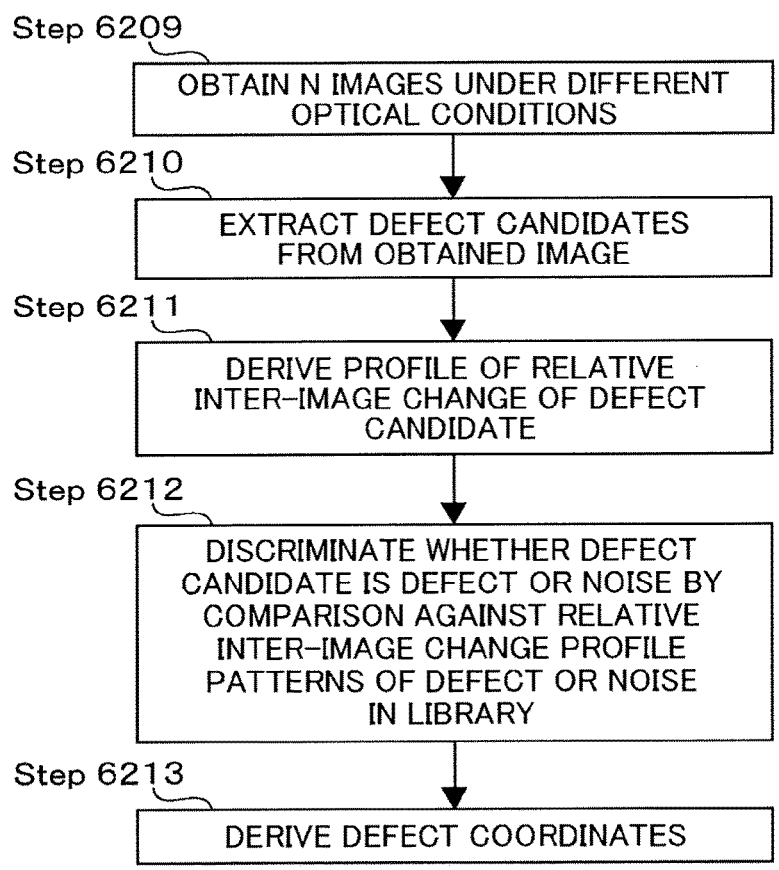
FIG. 6 is a flowchart explaining an example of a procedure for discriminating a defect from noise according to an embodiment of the present invention.

Then, using FIG. 6, a description is provided about a processing flow in which a bright point which is a defect candidate is derived from multiple images obtained with an optical condition being varied and discrimination is made as to whether the bright point is a defect or noise.

A first step is obtaining multiple images under different optical conditions by imaging a region under measurement on a sample 101 with the optical microscope 105 and the imaging element 207 (Step 6209). A next step is extracting a defect candidate using any one of the images obtained (Step 6210). A next step is deriving a profile of relative inter-image change of a bright point as a defect candidate extracted using the one image (Step 6211). A step that follows is comparing the profile of relative inter-image change obtained for each defect candidate with the profiles of relative inter-image change of defects or noises previously stored in a library and discriminating whether a bright point as a defect candidate is a defect or a noise (Step 6212). A final step is deriving the coordinates of a defect candidate determined as a defect (Step 6213).

Then, a description is provided about a case where height is selected as an optical condition to be varied and a case where directions of polarization for detection are selected as an example of deriving defect candidates.

Figure 7:
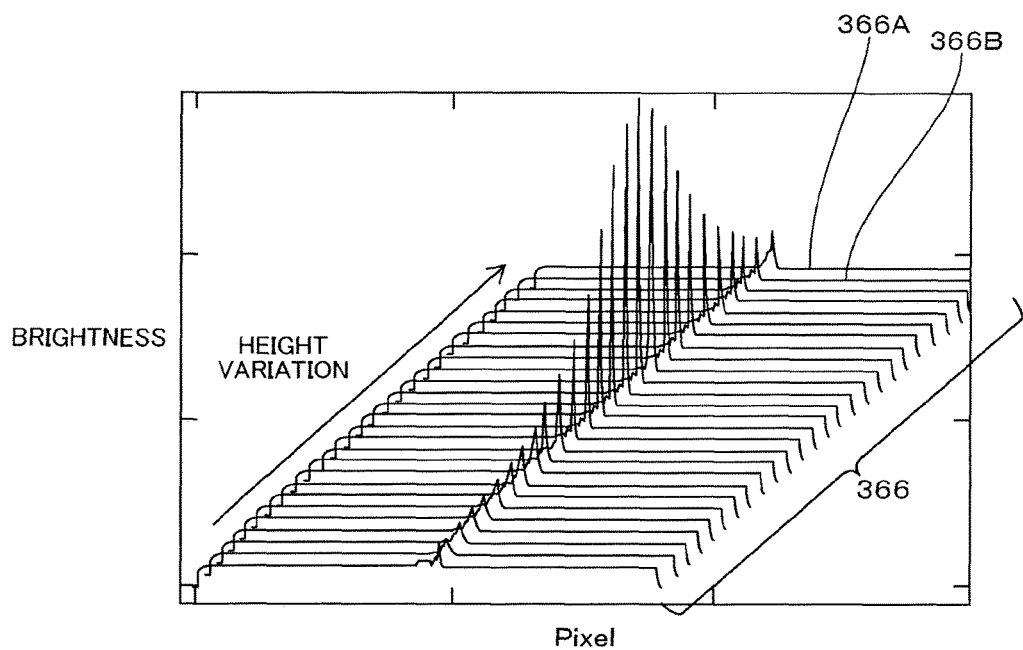
FIG. 7 is a diagram explaining signal value change depending on height variation with regard to defect scattering light.
Figure 8:
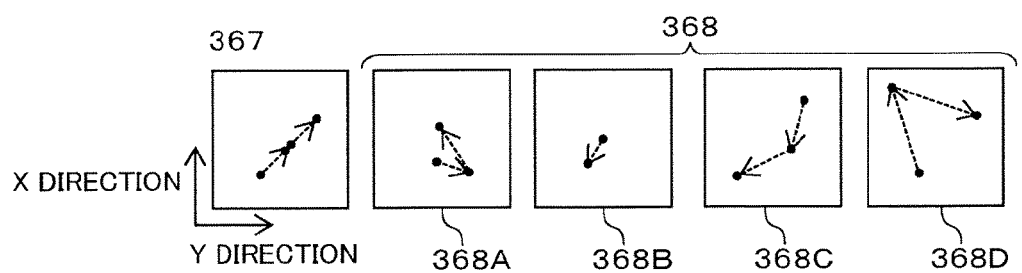
FIG. 8 is a diagram explaining an example of discriminating a defect from roughness according to an embodiment of the present invention.

Using FIGS. 7 and 8, a description is provided about an example of a case where height is selected as an optical condition to be varied. Possible ways of varying height are changing the height of the object lens and displacing the stage in a height direction. FIG. 7 is an example of change of a signal from defect scattering light when height is varied. Waveforms 366A, 366B are those extracted from dark-field images obtained with different heights. In multiple waveforms 366 obtained with different heights, the brightness value of defect scattering light undergoes a change close to a normal distribution depending on height variation, as depicted in FIG. 7.

On the other hand, the brightness value of roughness scattering light does not do so and changes variously. From a tendency of change of the brightness value depending on height variation, defect scattering light can be identified. By utilizing change of the position of a bright point when height is varied, as described previously, it is also possible to discriminate a defect from roughness. If the optical system for detection is the one in which the influence of aberration of the optical system is small, the center of gravity of brightness of a defect is nearly unchanged even when height is varied. But this is not true for roughness. In this regard, examples of directions in which a bright point moves and its displacements (images 368) in three images obtained with height being varied are depicted in FIG. 8. An image 367 represents a defect scattering light image and images 368 represent a bright point derived from a roughness scattering light image, respectively.

A defect scattering light image makes a regular movement as presented in the image 367, whereas roughness scattering light images make various movements as presented in the images 368. For example, as in images 368A, 368C, and 368D, when they make different movements from the movement of the defect scattering light image in the image 367, the bright point may disappear as in an image 368B in some height condition. In the optical system for detection, where there is aberration, the position and shape of a defect scattering light image may change depending on height variation and a direction and amount of change of the position and a tendency of change of the shape depend on defect conditions. However, this is not true for roughness images.

Figure 9:
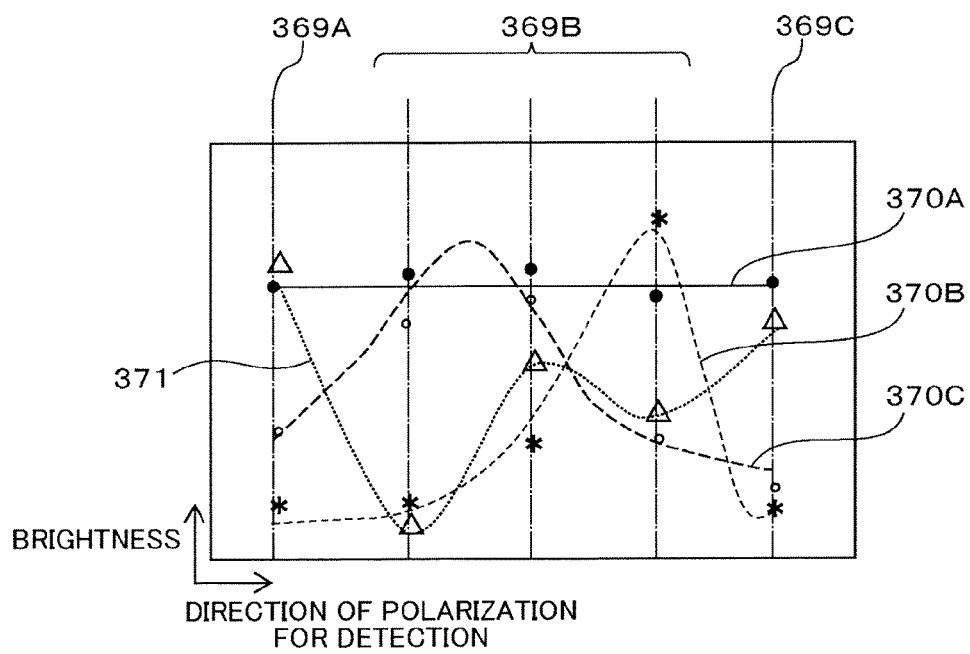
FIG. 9 is a diagram explaining an example of discriminating a defect from roughness according to an embodiment of the present invention.

Using FIG. 9, a description is provided about an example of a case where polarization for detection is selected as an optical condition to be varied.

A possible way of varying polarization for detection is continuously rotating a linear polarizer disposed on the optical axis of the optical system for detection. Multiple optical conditions should be obtained including X-polarized light, Y-polarized light, and polarization directions interpolating between the X-polarized light and Y-polarized light.

FIG. 9 is a diagram plotting examples of brightness changes in dark-field images obtained with X-polarized light (a line 369A), Y-polarized light (a line 369C), and three polarization direction (lines 369B) interpolating between the X-polarized light and Y-polarized light. A line 370A represents a brightness change of light scattering from a fine foreign material. Because light scattering from a fine foreign material is composed mainly of radially polarized light, its brightness is substantially constant, nearly independent of the directions of polarization for detection, when linear polarization is detected. Lines 370B and 370C represent examples of brightness changes of images made by light scattering from defects other than the fine foreign material.

Defect scattering light makes a regular movement depending on optical condition variation, as indicated by the lines 370B and 370C, whereas a roughness scattering light image makes an irregular movement which varies erratically, as indicated by the line 371. By utilizing this difference, it is possible to discriminate between roughness scattering light and defect scattering light. In FIG. 9, if images obtained under only two conditions of X-polarized light (line 369A) and Y-polarized light (line 369C) are used, it is impossible to discriminate between defect scattering light 370A and roughness scattering light 371. The accuracy of discrimination can be enhanced by using dark-field images obtained with additional optical conditions 369B interpolating between the two conditions.

As described above, it is possible to discriminate a defect from noise from change of an inter-image characteristic quantity in images made by defect scattering light and roughness scattering light under different optical conditions resulting from varying some optical condition. The foregoing discrimination methods are exemplary and discrimination methods are not limited to these methods.

Then, a description is provided about positioning alignment for determining the same location on a sample when deriving an inter-image characteristic quantity. If an optical condition to be varied does not cause a view field shift, positioning alignment is not required. If an optical condition to be varied causes a view field shift, inter-image positioning alignment is required. Optical conditions that do not cause a view field shift are those relevant to the illumination optical system, such as illuminating light intensity, illuminating light polarization, and illuminating light incident angle. Optical conditions that cause a view field shift are those relevant to the optical system for detection, such as spatial displacement, e.g., displacements in height and horizontal directions and polarization for detection. If a pattern is present within the view field, positioning alignment can be performed using the pattern. If a pattern is not present within the view field or for a wafer without patterns, one possible way is to measure in advance a view filed shift amount depending on optical condition variation, using a standard particle or standard pattern, and store the measurement as a parameter specific to the apparatus.

Another available way is to use a target region on a sample for detection, derive a view field shift amount in each case, and determine the same location on the sample. In this regard, one available way is to derive a view field shift amount from the displacement of a bright point of a defect that is not buried in light scattering from roughness present on the sample for detection, or one alternative way is to derive a view field shift amount from a roughness scattering light distribution.

If a roughness scattering light distribution is used, one possible way is to make positioning alignment using normalized correlation (Equation 1) or the like. A roughness scattering light image has a component that changes sensitively to optical condition variation and a component that is insensitive to optical condition variation. Thought the use of this component that is insensitive to optical condition variation, positioning alignment can be performed.

$$R_{NCC} = \frac{\sum_{j=0}^{N-1}\sum_{i=0}^{M-1} I(i,j)T(i,j)}{\sqrt{\sum_{j=0}^{N-1}\sum_{i=0}^{M-1} I(i,j)^2 \times \sum_{j=0}^{N-1}\sum_{i=0}^{M-1} T(i,j)^2}} \quad (数\ 1)$$

The way of making positioning alignment using a roughness scattering light distribution, in which positioning alignment is performed using a region for review, has an advantage in which high accuracy of positioning alignment can be achieved even for a view field shift amount that is not reproducible. And it has another advantage in which highly accurate positioning alignment can be performed even if a pattern that can be used for positioning alignment or a defect that is not buried in roughness scattering light is not present in the vicinity of a region for review.

With FIG. 10, a description is provided about an example of a positioning alignment method using normalized correlation. N images are obtained under different optical conditions (Step 6011, Step 6102, Step 6103). After obtaining N images (Step 6102, YES), one of the N images is set as a reference image. A step that follows is selecting a region including a region for which positioning alignment is desired to be performed in the reference image (Step 6104). A step that follows is deriving a value of normalized correlation with the region selected in Step 6104 for other images than the reference image (using Equation 1) (Step 6105). A step that follows is driving a location with a maximum value of normalized correlation (Step 6106). A region with a maximum value of normalized correlation is the same region on a sample as the region selected in Step 6104.

Another method using a difference is also conceivable. As images that are used for positioning alignment, inter alia, dark-field images obtained or the images of low-frequency components of spatial frequencies of dark-field images may be used. Instead of using a value of normalized correlation, a region with a value of the smallest difference from a region selected in Step 6104 may be taken as the same region image on a sample as the region selected in Step 6104. It is also allowed to use a matching pattern and a discrimination boundary without making positioning alignment and including a view field shift amount.

Then, a description is provided about focusing. As a focusing method, if a pattern or a defect scattering light image that is not buried in roughness scattering light is present within or in the vicinity of a scope for inspection, focusing is performed using its brightness value change. However, if there is not a pattern that can be used for focusing or a defect that is not buried in roughness scattering light, focusing is performed using a roughness scattering light distribution or using other height measurement means. Other measurement means include, inter alia, a height measurement means of a slit light projection type.

Then, a description is provided about a pupil filter. A pupil filter is an optical filter that preferentially transmits defect scattering light and blocks out roughness scattering light and that is disposed on or near the pupil plane of the optical system for detection for boosting the ratio of defect scattering light to roughness scattering light, which is described in Japanese Unexamined Patent Application Publication No. 2011-106974. Also in the present invention, a pupil filter can be used and has an optical characteristic in which it selectively transmits light in a region on the pupil plane and a polarization that make a large difference between defect scattering light and roughness scattering light in terms of their sensitivity to an optical condition being varied.

Figure 11:
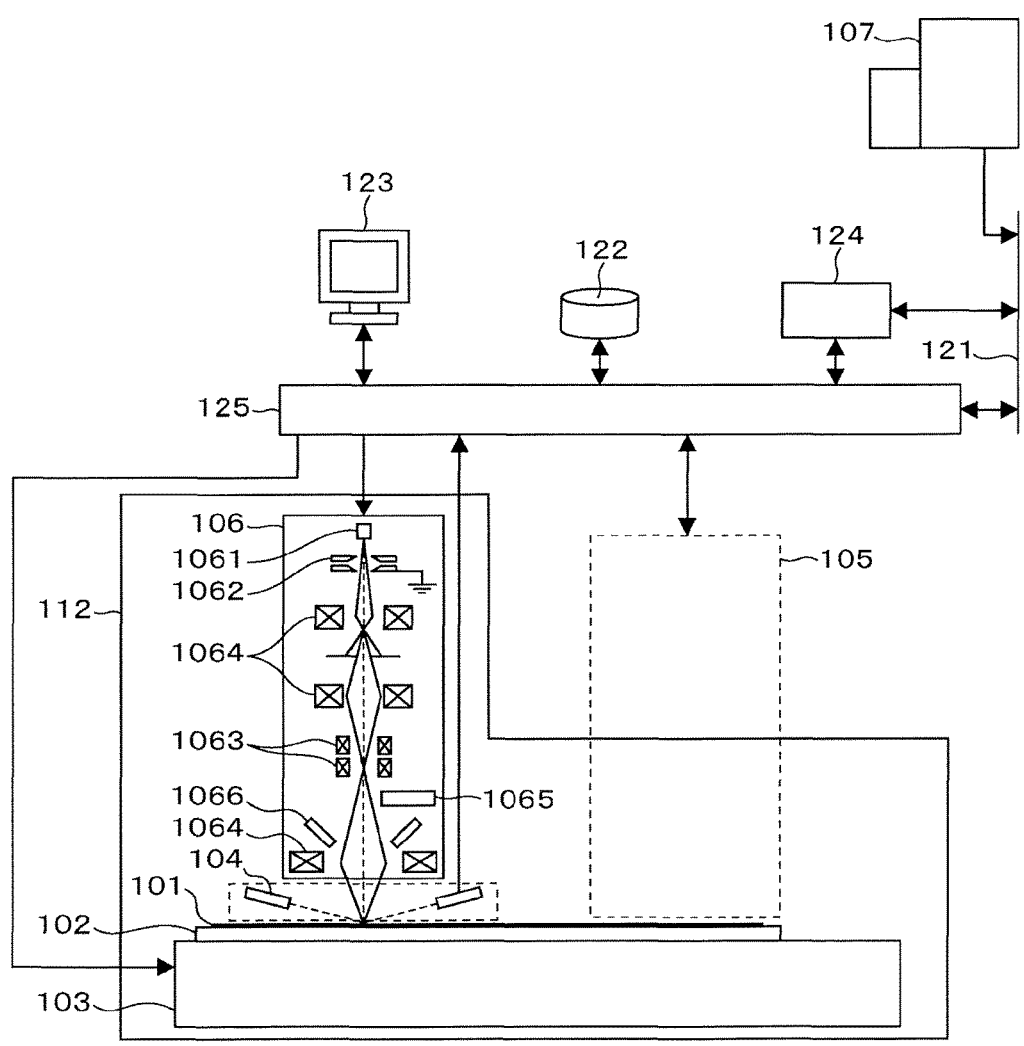
FIG. 11 is a structural diagram depicting an example of structure of an apparatus for reviewing a defect according to an embodiment of the present invention.

Next, an example of structure of a reviewing apparatus 100 equipped with the optical microscope 105 (FIG. 1) according to the present invention for coordinate alignment is depicted in FIG. 11.

The reviewing apparatus of the present embodiment includes a sample holder 102 on which a sample 101 for inspection is mounted, a stage 103 which moves the sample holder 102 so that the entire surface of the sample 101 can move to beneath a scanning electron microscope 106 (hereinafter referred to as SEM), the SEM 106 for detailed review of the sample 101, an optical height detection system 104 which detects the height of the surface of the sample 101 to allow the SEM 106 to focus on the surface of the sample 101, the optical microscope 105 which optically detects a defect on the sample 101 and obtains detailed position information of the defect on the sample 101, a vacuum chamber 112 which houses the SEM 106 and the object lens of the optical microscope 105, a control system 125 which controls the SEM 106, optical height detection system 104, and optical microscope 105, a user interface 123, a library 122, a network 121 for connection to a host system such as an inspection apparatus 107, and a storage device 124 which stores, inter alia, external data from the inspection apparatus 107 and provides data to the control system.

The SEM 106 is configured including the following internal components: an electron beam source 1061; an extraction electrode 1062 which extracts and accelerates beams of primary electrons emitted from the electron beam source 1061; a deflection electrode 1063 which controls the trajectory of the primary electron beams extracted and accelerated by the extraction electrode 1062; an object lens electrode 1064 which converges the primary electron beams whose trajectory is controlled by the defection electrode 1063 onto the surface of the sample 101; a secondary electron detector 1065 which detects secondary electrons emitted from the sample 101 irradiated with the converged primary electron beam after being subjected to trajectory control, a reflection electron detector 1066 which detects electrons with relative high energy such as reflection electrons emitted from the sample 101 irradiated with the converged primary electron beam, etc.

The optical microscope 105 includes an illumination optical system 201 which illuminates light obliquely to the sample 101, a condensing optical system 210 which collects light scattered above the sample 101 which is a part of scattering light emitted from the surface of the sample 101, and a detector 207 which detects scattering light from the sample 101, collected by the condensing optical system.

The control system 125 includes a SEM controller 1251 which controls the SEM 106, an optical microscope controller 1252 which controls the optical microscope, and an overall controller 1256 which controls the overall reviewing apparatus 100.

The stage 103, optical height detection system 104, optical microscope 105, SEM 106, user interface 123, library 122, and storage device 124 are connected to the control system 125 and the control system 125 is connected to a host system (e.g., inspection apparatus 107) through the network 121.

In the reviewing apparatus 100 configured as described above, particularly, the optical microscope 105 has a function of re-detecting (hereinafter referred to as detecting) a defect on a sample 101 detected by the inspection apparatus 107, using information representing the position of the defect detected by the inspection apparatus 107. The optical height detection system 104 has a function as means for primary electron beam focusing to converge primary electron beams of the SEM 106 onto the surface of a sample 101. The control system 125 has a function as means for position correction to correct information representing the position of a defect detected through inspection by another inspection apparatus, based on information representing the position of the defect detected by the optical microscope 105. The SEM 106 is configured to have a function of reviewing a defect whose position information is corrected by the control system 125. The stage 103 with a sample 101 mounted on it moves between the optical microscope 105 and the SEM 106, so that a defect detected by the optical microscope 105 can be reviewed by the SEM 106.

Figure 12:
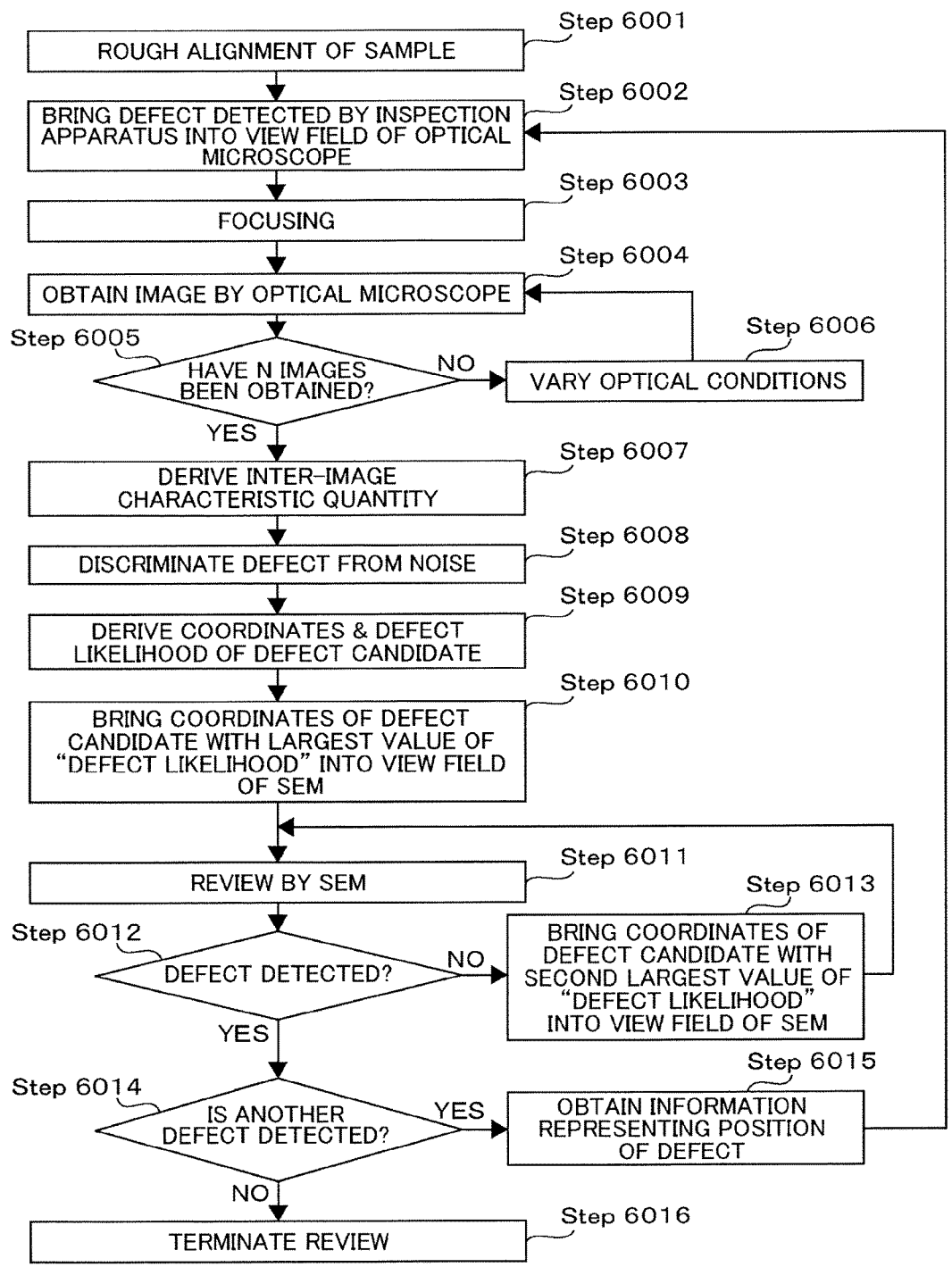
FIG. 12 is a flowchart explaining a procedure for reviewing a defect by the apparatus for reviewing a defect according to an embodiment of the present invention.

An example of a processing flow for defect review is described with FIG. 12. A first step is making a rough alignment of a sample 101. This is performed by bright-field review of the optical microscope 105 (Step 6001). A next step is moving the stage 103 to bring a defect on a sample 101 into the view field of the optical microscope 105 (Step 6002), in which the defect is desired to be reviewed by the reviewing apparatus 100, using information representing the position of the defect detected by another inspection apparatus 107, based on the defect coordinates obtained by the inspection apparatus 107. A next step is focusing, while moving the object lens 202 by the height control mechanism 209 (Step 6003). A next step is obtaining an image by the optical microscope 105 and the imaging element 207 (Step 6004).

N images are obtained by the optical microscope 105 and the imaging element 207, while an optical condition is varied (Step 6006), until N images have been obtained under different conditions (Step 6005, if NO). Once N images have been obtained (Step 6005, YES), a step that follows is deriving an inter-image characteristic quantity using the N images (Step 6007), followed by discriminating a defect from roughness through the use of the derived inter-image characteristic quantity (Step 6008) and deriving the coordinates and a defect likelihood value of a defect candidate (Step 6009). If it is not required to detect another defect, defect detection by the optical microscope terminates. Steps that follow are bringing the coordinates of a defect candidate with the largest value of defect likelihood into the view field of the SEM 106 (Step 6010) and carrying out review (Step 6011). Then, if a defect is present within the view field of the SEM, the processing proceeds to review of another defect (Step 6014, YES) or the review by SEM terminates (Step 6016).

If a defect is not present at the coordinates of a defect candidate with the largest value of defect likelihood (Step 6012, NO), steps that follow are bringing the coordinates of a defect candidate with the second largest value of defect likelihood into the view field of the SEM 106 (Step 6013) and carrying out review by SEM (Step 6011). These steps are repeated until a defect has been detected or until finding no defect candidate with a value of defect likelihood at or above a certain threshold. If no defect candidate with a value of defect likelihood at or above the threshold is found and no defect has been detected, the processing outputs a result that no defect is present within the view field of review (false information).

A result that a defect has been reviewed by SEM (Step 6012, YES) is sent to the control system 125 and registered into a database 122. If there are a large number of defects to be reviewed, some representative ones of them should be selected and detected/reviewed. Based on information representing the position of a defect, each of the selected defects which are detected beforehand by another inspection apparatus 107, and information representing the position of the corresponding defect detected by the optical microscope 105, a quantity of difference between the defect position (information) detected beforehand by another inspection apparatus and its position within the view field of the SEM 106 should be obtained. Using information representing thus obtained difference quantities for each of the representative defects, correction should be made of position information on defects other than the representative ones, not subjected to detection by the optical microscope 105, obtained through the detection by another inspection apparatus 107 beforehand.

Then, if information on another defect is required (Step 6014, YES), a step of obtaining information representing the position of a defect desired for review from the results of output of another inspection apparatus 107 is performed (Step 6015). Then, a return is made to the above step of bringing the defect into the optical microscope 105 and further processing is performed. If no defect has been detected through the foregoing defect detection procedure, there is a possibility that a defect is out of the view field of the optical microscope 105. Thus, a defect in an area circumjacent to the view field of the optical microscope 105 may be looked for; when doing so, after moving the sample 101 by a distance corresponding to the view field, processing should be performed according to the foregoing defect detection procedure; when not doing so, processing should be carried out according to the procedure.

Results of SEM review can be quickly fed back to the operation for setting the parameters for variation of an optical condition to be varied when obtaining images or setting a matching pattern and a discrimination boundary for discriminating a defect from roughness and the accuracy of discrimination can be enhanced efficiently.

While the invention made by the present inventors has been described specifically based on its embodiments hereinbefore, it will be appreciated that the present invention is not limited to the described embodiments and various modifications may be made thereto without departing from the scope of the invention.

Therefore, to solve the problems of related art, the present invention provides a method that uses multiple images obtained under multiple optical conditions, visualizes a defect, and derives the coordinates of the defect as well as an apparatus for reviewing a defect and a defect detection apparatus equipped with components implementing this method.

It is possible to visualize fine defects that have so far been undetectable, buried in roughness scattering light. When a defect that is detected by an optical defect inspection apparatus is reviewed in detail by SEM or the like, it is possible to bring a fine defect for review reliably into the view field for review of the SEM or the like and it is possible to enhance throughput of detailed inspection of defects through the use of the SEM or the like.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

What is claimed is:

1. A method for reviewing a defect comprising:
    illuminating a sample with light under a plurality of optical conditions, while varying only at least one condition of respective pluralities of illumination conditions, sample conditions, or detection conditions;
    detecting a plurality of lights scattering from the sample;
    obtaining multiple images of the sample under the plurality of different optical conditions while varying the at least one condition;
    obtaining a plurality of signals based on the plurality of lights detected;
    deriving a relative inter-image change of a characteristic quantity obtained from each image; and
    discriminating a defect from noise according to the characteristic quantity, the characteristic quantity being a waveform characteristic quantity, an image characteristic quantity, or a value characteristic quantity created using the relative inter-image change based on the plurality of signals; and
    determining coordinates of the defect.

2. The method for reviewing a defect according to claim 1,
    wherein detecting the plurality of lights includes a bright point of light scattering from a defect on the sample.

3. The method for reviewing a defect according to claim 1,
    wherein detecting the plurality of lights includes detecting the plurality of lights at different heights relative to the sample.

4. The method for reviewing a defect according to claim 1,
    wherein detecting the plurality of lights includes using a plurality of predetermined optical conditions based on signals obtained beforehand through the use of a standard sample.

5. The method for reviewing a defect according to claim 1, further comprising:
    outputting a likelihood of a defect discriminated as the defect.

6. The method for reviewing a defect according to claim 1,
    wherein obtaining the plurality of signals detects the plurality of lights with varying angles of rotation of a polarizer.

7. An apparatus for reviewing a defect comprising:
    an optical microscope configured to illuminate a sample with light under a plurality of optical conditions, while varying only at least one of a condition of a plurality of illumination conditions, a plurality of sample conditions, or a plurality of detection conditions, and to detect a plurality of lights scattering from the sample, the optical microscope including an imaging optical system configured to obtain multiple images of the sample under different optical conditions while varying the at least one condition;

a signal processor configured to obtain a plurality of signals based on the plurality of lights detected; and a controller configured to derive a relative inter-image change of a characteristic quantity obtained from each image and to discriminate a defect from noise according to the characteristic quantity, the characteristic quantity being a waveform characteristic quantity, an image characteristic quantity, or a value characteristic quantity created using the relative inter-image change based on the plurality of signals, and then to determine coordinates of the defect.

8. The apparatus for reviewing a defect according to claim 7,
wherein the optical microscope detects a plurality of lights including a bright point of light scattering from a defect on the sample.

9. The apparatus for reviewing a defect according to claim 7,
wherein the optical microscope detects a plurality of lights with different heights relative to the sample.

10. The apparatus for reviewing a defect according to claim 7,
wherein the optical microscope detects a plurality of lights using a plurality of predetermined optical conditions based on signals obtained beforehand through the use of a standard sample.

11. The apparatus for reviewing a defect according to claim 7, further comprising:
a display that outputs a likelihood of a defect discriminated as the defect.

12. The apparatus for reviewing a defect according to claim 7,
wherein the optical microscope detects the plurality of lights with varying angles of rotation of a polarizer.

13. The apparatus for reviewing a defect according to claim 7,
wherein the controller performs an adjustment of parameters in an inspection recipe or an adjustment of a recipe for discriminating the defect from roughness.

14. The apparatus for reviewing a defect according to claim 7,
wherein the characteristic quantity including the relative inter-image change between a plurality of images based on the plurality of signals is a characteristic quantity created after positioning alignment performed using a roughness scattering light image.

15. The apparatus for reviewing a defect according to claim 7,
wherein the controller performs the positioning alignment using a correlation value or a difference of roughness scattering light.

* * * * *